US00PP24998P3

(12) United States Plant Patent
Zaias-Fast

(10) Patent No.: US PP24,998 P3
(45) Date of Patent: Oct. 21, 2014

(54) ***CHLOROPHYTUM* PLANT NAMED 'CH8104'**

(50) Latin Name: *Chlorophytum laxum*
Varietal Denomination: CH8104

(71) Applicant: Magaly Zaias-Fast, Coral Springs, FL (US)

(72) Inventor: Magaly Zaias-Fast, Coral Springs, FL (US)

( * ) Notice: Subject to any disclaimer, the term of this patent is extended or adjusted under 35 U.S.C. 154(b) by 128 days.

(21) Appl. No.: 13/694,343

(22) Filed: Nov. 20, 2012

(65) Prior Publication Data

US 2014/0143922 P1 May 22, 2014

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Kent L Bell

(57) ABSTRACT

A new and distinct *Chlorophytum laxum* cultivar named 'CH8104' is disclosed, characterized very compact plant habit, with arching foliage. Foliage is colored green with a strong white margin and resists tearing and breakage. The new cultivar is a *Chlorophytum laxum* suitable as an indoor pot plant.

2 Drawing Sheets

Latin name of the genus and species: *Chlorophytum laxum.* Variety denomination: 'CH8104'.

BACKGROUND OF THE INVENTION

The new cultivar is a chance, whole plant mutation selected by the inventor, Magaly Zais-Fast, a citizen of the United States, in 2002 at a commercial greenhouse located near Apopka, Fla. 'CH8104' was found as a single, naturally occurring, whole plant mutation growing in a commercial planting of the parent variety, an unnamed variety of *Chlorophytum laxum.*

Asexual reproduction of the new cultivar 'CH8104' was first performed by divisions at a non-commercial nursery in Florida during 2002. The inventor kept the plants in a confidential, restricted location, observing plant habit and stability. These plants showed that the unique features of this cultivar are stable and reproduced true to type. In August of 2012, 'CH8104' was reproduced by micro-propagation.

SUMMARY OF THE INVENTION

The cultivar 'CH8104' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CH8104'. These characteristics in combination distinguish 'CH8104' as a new and distinct *Chlorophytum* cultivar:

1. Very compact plant habit.
2. Arching foliage habit.
3. Suitability as an indoor pot plant.
4. Strong foliage resistant to tearing and breakage.
5. Strong green coloration of the center of the leaf blade, and thick white margin coloration.

PARENT COMPARISON

Plants of the new cultivar 'CH8104' are similar to plants of the unpatented, unnamed, parent variety, *Chlorophytum laxum* in most horticultural characteristics, however, plants of 'CH8104' are much shorter and more compact than the parent variety. Additionally the foliage of 'CH8104' has a thicker white margin than the parent variety, and the plants of the parent variety have been observed to flower, whereas the new variety does not flower freely.

COMMERCIAL COMPARISON

'CH8104' can be compared to the patented commercial variety *Chlorophytum laxum* 'Lemon Lime', unpatented. Plants of 'Lemon Lime' are similar to plants of 'CH8104' in most horticultural characteristics, however, plants of 'CH8104' is more compact, and do not produce flowers, as plants of 'Lemon Lime' have been observed to produce.

BRIEF DESCRIPTION OF THE PHOTOGRAPHS

Figure 1:
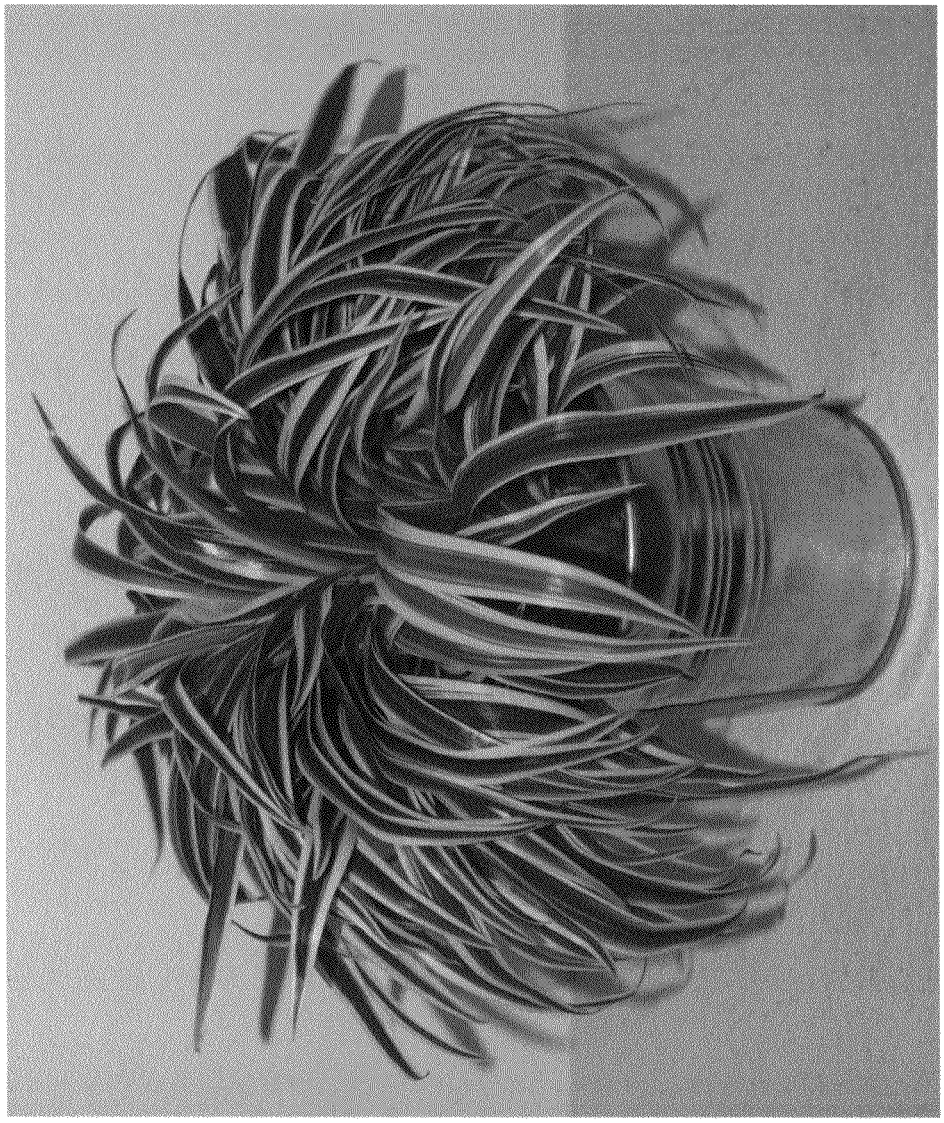

The accompanying photograph in FIG. 1 illustrates in full color a typical plant of 'CH8104' grown in a greenhouse. This plant is approximately 6 months old, shown in a 4 inch pot. The photograph was taken using conventional techniques and although colors may appear different from actual colors due to light reflectance it is as accurate as possible by conventional photographic techniques.

Figure 2:
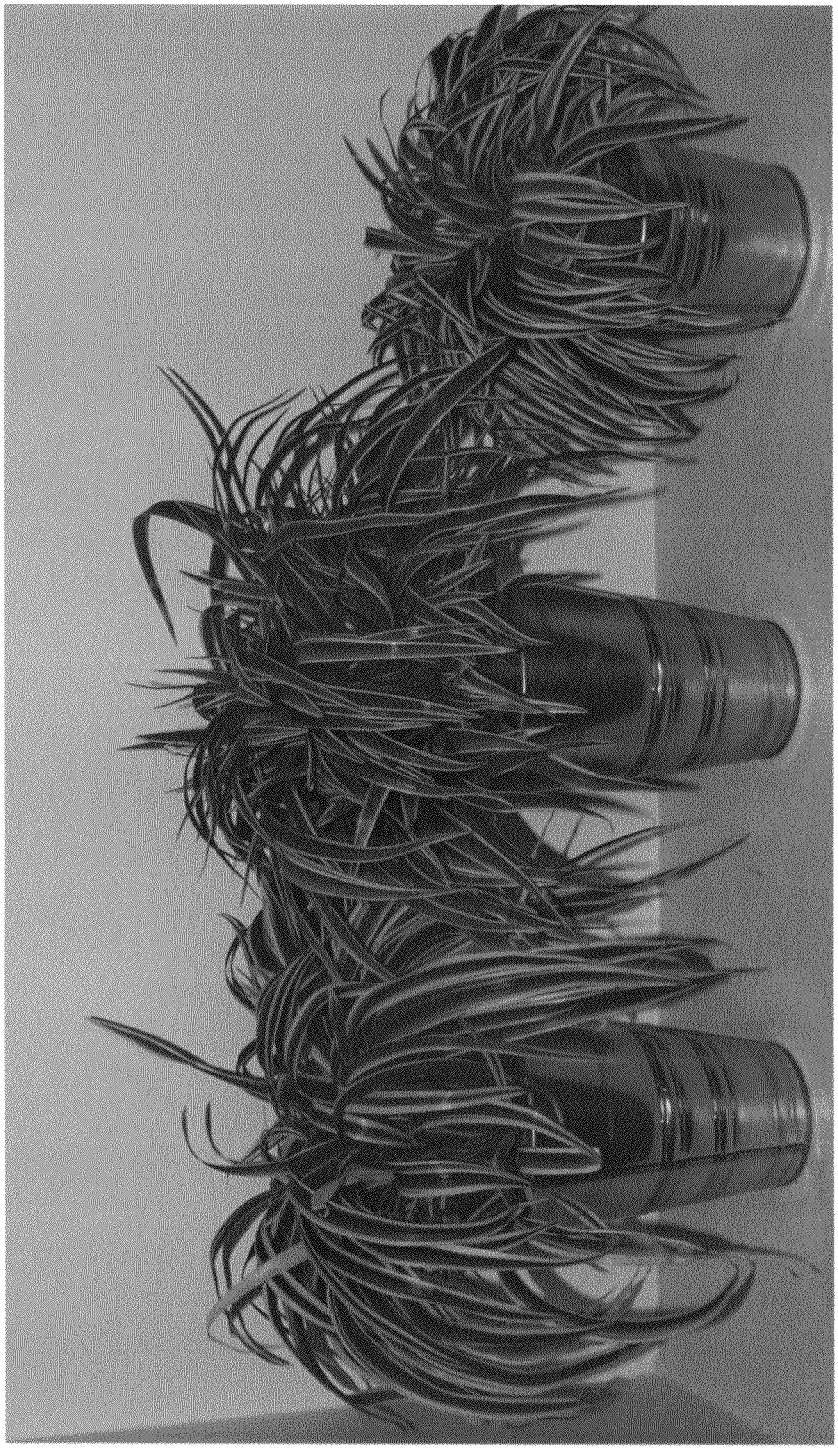

FIG. 2 illustrates in full color typical plants of the comparator variety, *Chlorophytum laxum* 'Lemon Lime', the parent variety, an unnamed *Chlorophytum laxum* and the new variety, 'CH8104'. The plant on the farthest left of the photo is *Chlorophytum laxum* 'Lemon Lime', the center plant is the parent variety, an unnamed *Chlorophytum laxum.* The plant on the farthest right of the photo is the new variety, 'CH8104'. Plants are all the same age, demonstrating the shorter, more compact nature of the new variety.

DETAILED BOTANICAL DESCRIPTION

In the following description, color references are made to The Royal Horticultural Society Colour Chart, 2001 except where general terms of ordinary dictionary significance are used. The following observations and measurements describe 'CH8104' plants grown in a climate controlled greenhouse in Apopka, Fla. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Chlorophytum laxum* cultivar 'CH8104'.

PLANT

Growth habit: Tender indoor plant, with a mounding appearance.
Height: Approximately 17 cm.
Plant spread: Approximately 30 cm.
Normal pot size: 4 inch.
Growth rate: Moderate to slow.
Branching characteristics: Non-branching.
Number of leaves per plant: Approximately 110.
Age of plant described: Approximately 9 months.

FOLIAGE

Leaf:

*Arrangement.*—Rosette of single, sessile leaves.
*Average length.*—Approximately 17 cm.
*Average width.*—Approximately 1.8 cm.
*Shape of blade.*—Linear.
*Aspect.*—Heavily arched, very slightly undulating of youngest foliage.
*Apex.*—Acute.
*Base.*—Linear, very slightly tapered, ending directly in soil.
*Margin.*—Entire.
*Texture of top surface.*—Smooth, moderately glossy.
*Texture of bottom surface.*—Smooth, moderately glossy.
*Color.*—Young foliage upper side: Near R.H.S. Green 141B, margin and some interior stripes colored near Yellow-Green 154D. Young foliage under side: Near R.H.S. Green 141C, margin and some interior stripes colored near Yellow 2D. Mature foliage upper side: Near R.H.S. Green 137A, margin and some interior stripes colored near White 155D. Mature foliage under side: Near R.H.S. Green 137B, margin and some interior stripes colored near White 155D.
*Venation.*—Type: Pinnately parallel. Venation coloration: Indistinguishable from leaf blade coloration.
*Other foliage characteristics.*—Strong foliage resists tearing and breakage during transport and other potential mechanical damage.

Petiole: Not present.

INFLORESCENCE

Flowers not observed in this cultivar.

OTHER CHARACTERISTICS

Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed, as the variety has been only tested as an indoor ornamental potted plant.
Fruit/seed production: Not observed.

What is claimed is:

1. A new and distinct cultivar of *Chlorophytum laxum* plant named 'CH8104' as herein illustrated and described.

* * * * *